United States Patent [19]
Christie et al.

[11] Patent Number: 5,824,060
[45] Date of Patent: Oct. 20, 1998

[54] NATURAL TISSUE HEART VALVE FIXATION

[75] Inventors: Grant W. Christie, Auckland, New Zealand; Carol E. Eberhardt, Fullerton, Calif.

[73] Assignee: Medtronic, Inc., Minneapolis, Minn.

[21] Appl. No.: 129,636

[22] Filed: Sep. 29, 1993

[51] Int. Cl.⁶ ...................................................... A61F 2/24
[52] U.S. Cl. ............................................................... 623/2
[58] Field of Search .................... 623/2, 3; 8/94, 8/11

[56] References Cited

U.S. PATENT DOCUMENTS

| | | | |
|---|---|---|---|
| 3,966,401 | 6/1976 | Hancock et al. | 623/2 |
| 4,050,893 | 9/1977 | Hancock et al. | 623/2 |
| 4,090,878 | 5/1978 | Hancock et al. | 623/2 |
| 4,247,292 | 1/1981 | Angell | 623/2 |
| 4,350,492 | 9/1982 | Wright et al. | 623/2 |
| 4,372,743 | 2/1983 | Lane | 623/2 |
| 4,443,895 | 4/1984 | Lane | 623/2 |
| 4,624,822 | 11/1986 | Arru et al. | 623/2 |
| 4,800,603 | 1/1989 | Jaffe | 623/2 |

FOREIGN PATENT DOCUMENTS

| | | | |
|---|---|---|---|
| 1228203 | 10/1987 | Canada | 623/2 |
| 0165622 | 12/1985 | European Pat. Off. | 623/2 |
| 0402036 | 12/1990 | European Pat. Off. | 623/2 |
| 0402176 | 12/1990 | European Pat. Off. | 623/2 |
| 1510163 | 5/1978 | United Kingdom | 623/2 |
| 2169386 | 7/1986 | United Kingdom | 623/2 |
| 9014804 | 12/1990 | WIPO | 623/2 |
| 9304643 | 3/1993 | WIPO | 623/2 |

OTHER PUBLICATIONS

Butterfield et al. "Improved Outlet Geometry and Function in Porcine BioProsthetic Heart Valves: The Next Generation" Apr. 1992, p. 82.

Butterfield et al. "Hydrodynamic Function of Second Generation Porcine Bioprosthetic Heart Valves" Dec. 1991 Journal of Cardiac Surgery vol. 6, No. 4, 1991.

Barratt–Boyes et al. "The Stentless Bioprosthesis=Surgical Challenges & Implications for Long Term Durability" European Journal of Cardio–thoracis Surgery 1992 S.39–S.43.

*Primary Examiner*—Robert A. Clarke
*Attorney, Agent, or Firm*—Harold R. Patton; Curtis D. Kinghorn; Peter Forrest

[57] ABSTRACT

A natural tissue heart valve includes a tubular wall having an outflow section and valve leaflets which allow flow into the outflow section. A heart valve of this type is subjected to a fixative fluid to provide a first differential fluid pressure across the tubular wall of the outflow section and a second differential fluid pressure across the valve leaflets. The first differential fluid pressure acts outwardly on the tubular wall, and the differential pressures are unequal.

29 Claims, 3 Drawing Sheets

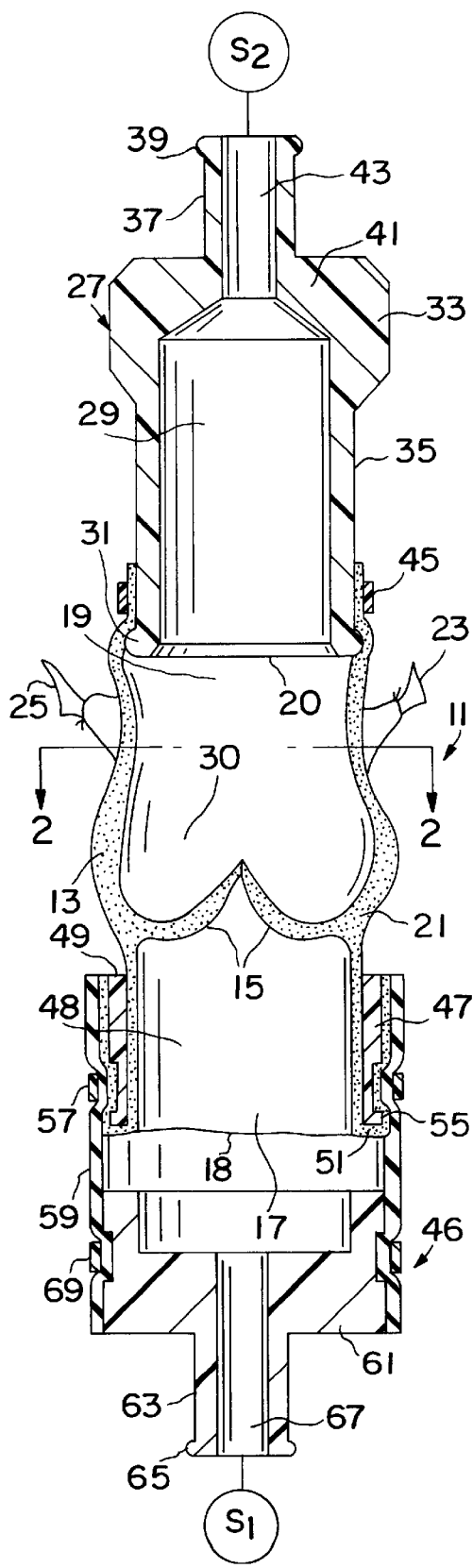
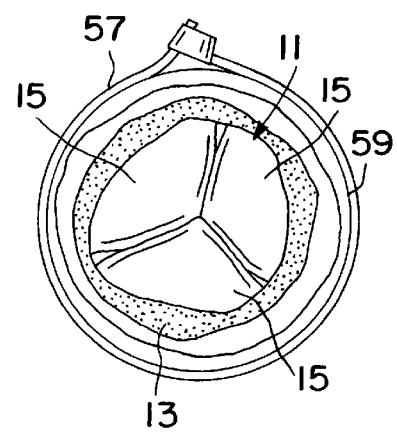
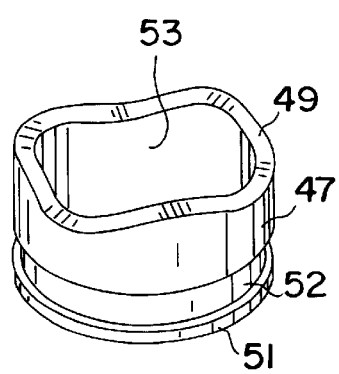

NATURAL TISSUE HEART VALVE FIXATION

BACKGROUND OF THE INVENTION

This invention relates to a method of fixing natural tissue heart valves.

Animal heart valves, such as porcine heart valves, are commonly used as an implant in humans to replace a natural human heart valve. Before the animal heart valve can be used as an implant, it must undergo processing to make it suitable for human use. One important step in the processing of animal heart valves is fixation, i.e., stabilizing the tissue against degradation.

A natural tissue animal or human heart valve includes a tubular wall defining a passage and valve leaflets dividing the passage into an inflow section leading to the leaflets and an outflow section leading away from the leaflets. The leaflets are openable to allow flow from the inflow section to the outflow section in response to a differential pressure across the leaflets tending to force them toward the outflow section.

After harvesting, the circumferential dimensions of the tubular wall of the inflow and outflow sections of the heart valve reduce as a result of the valve going to a relaxed, i.e., unpressurized state. The tubular wall of the outflow section which in the case of an aortic valve is the aortic root must be expanded radially outwardly to near its original dimensions, i.e., to a size compatible with its natural physiological state, and then fixed in that condition so it will not thereafter shrink or partially collapse radially inwardly. In order to expand the outflow section as desired, it is necessary to have a differential fluid pressure acting across the tubular wall of the outflow section in a radial outward direction sufficient to achieve the desired expansion during a suitable time period. Although the desired differential pressure for this task may vary over a wide range, the outwardly acting differential pressure is presently often in the range of from about 20 mm Hg to about 120 mm Hg.

Another consideration in the fixation process is the differential fluid pressure to which the valve leaflets are to be subjected. The differential pressure across the leaflets can vary widely depending upon the school of thought of the scientists involved and other factors. However, it is generally believed desirable to fix the valve leaflets with low or no differential fluid pressure acting across them. For example, the differential fluid pressure acting across the valve leaflets in a direction from the inflow section to the outflow section, may be from about 0 mm Hg to about 4 mm Hg.

The problem is that the pressure requirements for the leaflets and for the tubular wall of the outflow section may be very different, and in actual practice, the pressures required for tubular wall expansion are normally much greater than the pressures desired for the valve leaflets. If the valve leaflets are fixed at the higher pressures required for the tubular wall of the outflow section, the collagen waveforms of the leaflets tend to stretch to the extent that the leaflets become undesirably stiff. On the other hand, the low pressures desired in valve leaflet fixation are insufficient to expand the tubular wall of the outflow section as desired.

SUMMARY OF THE INVENTION

The present invention solves this problem by subjecting the tubular wall of the outflow section and the valve leaflets to different differential fluid pressures. This enables the differential fluid pressures for the tubular wall of the outflow section and for the valve leaflets to be independently selected. Consequently, each of these differential fluid pressures can be selected to achieve the desired results on the tubular wall of the outflow section and on the valve leaflets. In addition, this invention reduces the distortion of a natural tissue heart valve which is inherent in prior art fixation techniques.

With this invention, a natural tissue heart valve is fixed by subjecting the valve to a fixative fluid to provide a first differential fluid pressure across the tubular wall of the outflow section and a second differential pressure across the valve leaflets. The first differential pressure acts outwardly on the tubular wall, and the differential pressures are unequal.

This fixative fluid may be any fluid, either liquid or gas, which is suitable for fixing a natural tissue heart valve. At present, a glutaraldehyde solution is preferred.

In a broad sense, this invention is not dependent upon the particular differential fluid pressures employed. However, in a preferred practice of the method, the first differential fluid pressure is sufficient to enlarge the tubular wall of the outflow section. Ordinarily, the first differential fluid pressure, which acts across the tubular wall of the outflow section, is greater than the second differential fluid pressure, which acts across the valve leaflets. For many applications, the first differential fluid pressure is preferably in the range of from about 20 mm Hg to about 80 mm Hg. For a porcine aortic heart valve, the first differential pressure is preferably in the range of from about 20 mm Hg to about 50 mm Hg, with 40 mm Hg being considered optimum. The second differential pressure, which acts across the valve leaflets, is preferably low and in the range of from about 0 mm Hg to 4 mm Hg, with a differential pressure of substantially 0 mm Hg being considered optimum.

This invention also provides for varying of the differential pressures during fixation. For example, the second differential pressure may be varied in a way to cause opening and closing of the valve leaflets. This results in the flowing of some of the fixative fluid through the valve leaflets.

Although the method may be carried out in different ways, in one preferred technique, the fixative fluid under pressure is supplied to the inflow and outflow sections through separate openings in these sections. Thus, the inflow and outflow sections are coupled to fixative fluid under pressure. Also, the valve is immersed in a bath of fixative solution. Preferably, fixative fluid is flowed into the inflow section and the outflow section with the pressure of the fixative fluid in the outflow section being greater than the pressure of the bath acting on the outside of the valve to provide the desired differential fluid pressure acting outwardly across the tubular wall of the outflow section.

The pressure of the fixative fluid in the inflow section is sufficient in relation to the pressure of the fixative fluid in the outflow section to create the desired differential fluid pressure across the valve leaflets. For example, by providing fixative fluid at 40 mm Hg in both the inflow and outflow sections, the differential fluid pressure acting across the tubular wall of the outflow section is about 40 mm Hg, and the differential fluid pressure acting across the valve leaflets is about 0 mm Hg.

The inflow and outflow sections may be coupled to the same or separate sources of fixative fluid under pressure. In one apparatus used to carry out the method of the invention, the inflow and outflow sections are coupled to first and second sources of fixative fluid, respectively.

Although the fixative fluid can be pressurized in different ways, this can be easily accomplished by controlling the static head height of the sources of the fixative fluid in relation to the heart valve. With this invention, the pressure of the fixative fluid supplied by one or both of the sources to the associated section can be changed as by changing the static head height of the source.

The method of this invention is applicable to the substantially simultaneous fixation of a plurality of natural tissue heart valves. This can be accomplished, for example, by coupling all of the inflow sections of the heart valves to a first manifold and all of the outflow sections of the heart valves to a second manifold. The exteriors of the valves are subjected to the action of a fixative fluid, and a fixative fluid under pressure is supplied through the first and second manifolds to the inflow and outflow sections, respectively, of the heart valves.

In order to better adapt the inflow and outflow sections of the heart valve to receive fixative fluid under pressure, it is preferred to attach end walls to the inflow and outflow sections to provide inflow and outflow chambers. Each of the end walls has an inlet leading to the associated chamber. With this arrangement, fixative fluid under pressure is flowed through each of the inlets to the associated chamber.

Generally, it is not desired to expand the tubular wall of the inflow section with the fluid under pressure. Accordingly, this invention provides for supporting the tubular wall of the inflow section against expansion as a result of the fixative fluid under pressure in the inflow section. Of course, the support need not be provided if expansion of the tubular wall of the inflow section is acceptable or if the tubular wall of the inflow section has sufficient strength to withstand the internal pressure without any, or any unacceptable, expansion. This is preferably accomplished by providing a support ring about the inflow section. For the fixation of an aortic valve, it is preferred to utilize a support ring which has a wavy edge positioned to support the annulus of the valve.

To attach the support ring to the valve, tissue of the valve is folded about an edge portion of the support ring, and the folded tissue is clamped between an elastomeric sleeve and the support ring. The end wall is coupled to the elastomeric sleeve. With this arrangement, the support ring forms a relatively rigid base against which the folded tissue can be clamped, and the elastomeric sleeve prevents the clamped tissue from being cut and also provides a resilient attachment for the end wall to the heart valve.

The invention, together with additional features and advantages thereof, may best be understood by reference to the following description taken in connection with the accompanying illustrative drawings.

BRIEF DESCRIPTION OF THE DRAWINGS

FIG. 1 is an axial, sectional view through a porcine aortic heart valve and associated fixtures with sources of fixative fluid under pressure being shown schematically.

FIG. 2 is a sectional view taken generally along line 2—2 of FIG. 1.

FIG. 3 is a perspective view of the support ring.

DESCRIPTION OF THE PREFERRED EMBODIMENT

Figure 4:
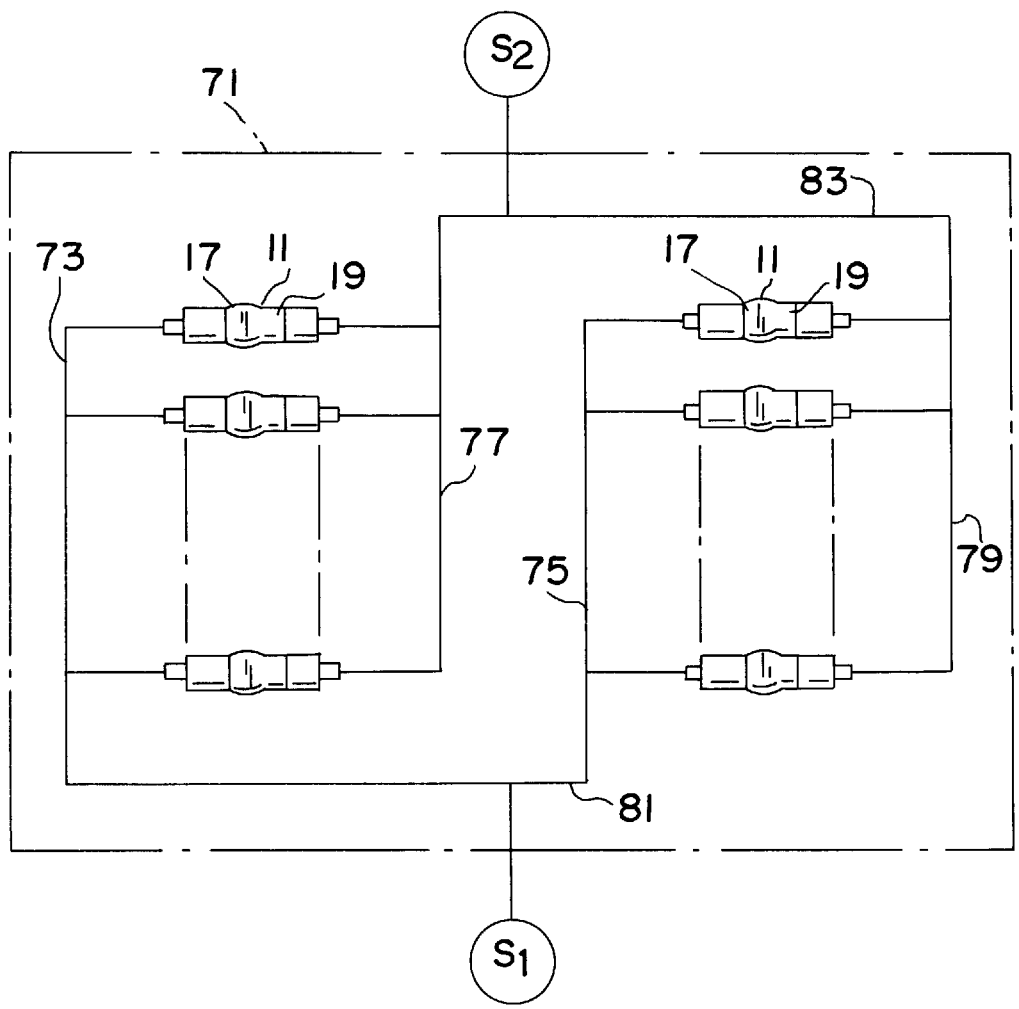
FIG. 4 is a schematic piping diagram illustrating a preferred apparatus for use in simultaneously fixing a plurality of heart valves.

FIG. 1 shows a porcine aortic heart valve 11 which includes a tubular wall 13 defining a passage and valve leaflets 15 dividing the passage into an inflow section 17 leading to the leaflets and an outflow section 19 leading away from the leaflets. The inflow section 17 and the outflow section 19 have openings 18 and 20, respectively, which, for the purposes of the fixation technique of this invention, may be regarded as inlets for fixation fluid. The leaflets 15 are openable to allow flow from the inflow section 17 to the outflow section 19 in response to a higher pressure in the inflow section than in the outflow section. The leaflets 15 are attached to the tubular wall near an annulus 21. The portion of the tubular wall 13 of the outflow section 19 is commonly referred to as an aortic root. As shown in FIG. 1, the valve 11 has been appropriately trimmed to make it suitable for fixation, and right and left coronaries 23 and 25 are tied off in a conventional manner. Although the valve 11 is a porcine aortic valve, it should be understood that the invention is not limited to aortic valves or to porcine heart valves and other natural tissue heart valves, both animal and human, can be fixed in accordance with the teachings of this invention.

The inflow section 17 and the outflow section 19 are coupled to sources of fixative fluid under a desired pressure $S_1$ and $S_2$ respectively. Although the sources $S_1$ and $S_2$ may be a single source, in this embodiment, the sources are separate. Although different fixative fluids may be used, it is preferred to utilize a glutaraldehyde solution as each of the sources of fixative fluid.

It is known to couple the outflow section 19 of an aortic natural tissue heart valve to a source of fixative fluid under pressure. Although this can be accomplished utilizing prior art techniques, if desired, it is preferred to utilize a tubular fixture 27 having an axial passage 29 extending therethrough. The fixture 27 cooperates with the outflow section 19 to provide an outflow chamber 30. The fixture 27, which is preferably constructed of a rigid polymeric material, such as Delrin, has an annular distal rib 31, a proximal shoulder 33 and a smooth, external, peripheral surface 35 which is preferably cylindrical extending between the shoulder 33 and the rib 31. The fixture 27 has a reduced diameter neck 37 which terminates proximally in a proximal rib 39. The fixture 27 is coupled to the source $S_2$ in any suitable manner, including the manner described hereinbelow.

The fixture 27 has an end wall 41 and an inlet 43 leading to the outflow section 19. Because of the smooth peripheral surface 35, the fixture 27 can be inserted to virtually any desired depth into the outflow section 19, and a conventional releasable clamping band 45 is applied around the tubular wall 13 just above (as viewed in FIG. 1) the rib 31 to clamp the tubular wall to the fixture. This variable depth of insertion feature varies the length of the overall assembly shown in FIG. 1 to facilitate mounting of this assembly as described more fully below.

One feature of this invention is coupling of the inflow section 17 to the source $S_1$ of fixative fluid under pressure. Although this can be accomplished in different ways, it is preferred to employ a fixture 46 which cooperates with the inflow section 17 to provide an inflow chamber 48. The fixture 46 includes a support ring 47 around the tubular wall 13 of the inflow section 17 to support the inflow section against expansion radially outwardly as a result of the fixative fluid under pressure applied to the inflow section. The support ring 47 is rigid and is preferably constructed of a rigid polymeric material, such as Delrin. Alternatively, the support ring 47 may be elastomeric so that is stretches within limits to limit the radial outward expansion of the tubular wall 13 of the inflow section 17. The support ring 47 has a scalloped or wavy distal edge 49, a proximal edge portion 51 and an annular groove 52 in or adjacent the proximal edge portion 51. A passage 53 (shown on FIG. 3) extends axially completely through the support ring 47.

When in position on the heart valve 11, the wavy edge 49 extends along the annulus 21 of the valve 11. Specifically, the wavy distal edge 49 is configured so as to generally conform to the configuration of the annulus 21 so that inflow section 17 will be supported by the support ring 47 against expansion radially outwardly.

Valve tissue, and in particular a region 55 of the tubular wall 13, is folded about the edge portion 51 of the support ring 47 as shown by way of example in FIG. 1. The fixture 46 also includes a conventional releasable clamping band 57 and an elastomeric sleeve 59, and the region 55 is clamped by the clamping band 57 between the elastomeric sleeve 59 and the support ring 47. The elastomeric sleeve 59 prevents the region 55 of tissue being cut by the relatively narrow clamping band 57, and the support ring 47 provides a rigid base against which to clamp the region of tissue. The clamping band 57 is in registry with the groove 52 and forces tissue of the region 55 into the groove to interlock with the support ring 47.

The fixture 46 includes an end wall 61 having a neck 63 which terminates in a rib 65 and which is suitably coupled to the elastomeric sleeve 59. The end wall 61 has an inlet 67 extending through the neck 63, and the fixture 46 includes a conventional releasable clamping band 69 which attaches the end wall to the elastomeric sleeve 59. The inlet 67 is coupled to the source $S_1$ so that fixative fluid under pressure from the source $S_1$ can flow through the inlet 67 to the inflow section 17.

It is apparent from FIG. 1 that the inflow section 17 and the outflow section 19 can each be subjected to fixative fluid under any desired fluid pressure to create different differential fluid pressures across the tubular wall 13 of the outflow section 19 and across the valve leaflets 15. Although these pressures can vary widely as described above, in a preferred embodiment, the fluid pressures in both the inflow section 17 and the outflow section 19 is about 40 mm Hg. This creates a 0 differential fluid pressure across the leaflets 15 and about a 40 mm Hg differential pressure acting outwardly across the wall 13 of the outflow section 19.

During the time that the pressures are applied from the sources $S_1$ and $S_2$ the exterior of the valve 11 is subjected to the action of a fixative fluid preferably by immersion of the valve in a bath of fixative solution as described below. In this event, the differential fluid pressure acting across the tubular wall 13 of the outflow section 19 is the difference between the hydrostatic pressure from the bath and the internal pressure from the source $S_2$. However, because of the shallow immersion, the differential pressure across the tubular wall 13 of the outflow section 19 is approximately equal to the internal pressure applied by the source $S_2$.

With these pressures applied, the tubular wall 13 is expanded by the internal pressure from its formerly shrunk or contracted condition and fixed in the expanded condition. The valve leaflets 15 are fixed under 0 differential pressure which means that the collagen waveform of the leaflets is not adversely altered, and the leaflets are not adversely stiffened. The tubular wall 13 of the inflow section 17 is prevented from expansion by the support ring 47, and the wavy distal edge 49 supports the annulus against expansion due to the internal pressure in the inflow section.

This invention is applicable to the simultaneous fixation of a plurality of natural tissue heart valves, and a preferred way to accomplish this is shown in FIG. 4. More specifically, FIG. 4 shows schematically in phantom lines a shallow tank 71, parallel inflow manifolds 73 and 75 and parallel outflow manifolds 77 and 79. The inflow manifolds 73 and 75 are coupled to an inflow header 81 which in turn is coupled to the source of fixative fluid under pressure $S_1$. Similarly, the outflow manifolds 77 and 79 are coupled to an outflow header 83 which in turn is coupled to the source of fixative fluid under pressure $S_2$. A first series of the valves 11 is coupled in parallel to the inflow manifold 73 and the outflow manifold 77, and a second series of the valves 11 is coupled in parallel to the inflow manifold 75 and the outflow manifold 79. More specifically, the inflow sections 17 of each of the valves 11 is coupled to an associated inflow manifold 73 and 75, and the outflow manifolds 19 of each of the valves 11 is coupled to an associated outflow manifold 77 and 79. The manifolds 73, 75, 77 and 79 and the headers 81 and 83 are provided within the tank.

Although various sequences of operation can be employed, in a preferred sequence, each of the valves 11 is assembled with associated fixtures 27 and 46 as shown in FIG. 1. This valve-fixture assembly is then coupled between an associated pair of the manifolds 73 and 77 or 75 and 79 as shown in FIG. 4. Next, the tank 71 is filled to an appropriate height with a glutaraldehyde fixative solution so as to immerse all of the valves 11, fixtures 27 and 46 and the manifolds in the fixative solution. Finally, fixative solution from the sources $S_1$ and $S_2$ is introduced to the inflow sections 17 and outflow sections 19, respectively, of the valves 11 through the associated headers and manifolds. The valves 11 are then subjected to the action of the fixative solution for a sufficient time to fix each of the valves with the fixation occurring substantially simultaneously for all of the valves. The length of time required will vary but may be, for example, about 24 hours to about 3 days.

The manifolds 73, 75, 77 and 79 are mounted in the tank 71 in fixed parallel relationship. It is important that each of the valve-fixture assemblies be of a length sufficient to be coupled to the associated pair of manifolds. The invention accomplishes this in two ways. First, each of the fixtures is coupled to the associated manifolds in a manner to accommodate valve-fixture assemblies of different lengths. Secondly, the length of the valve-fixture assembly can be varied as described above in connection with FIG. 1 by the degree to which the fixture 27 is inserted into the outflow section 19.

Figure 5:
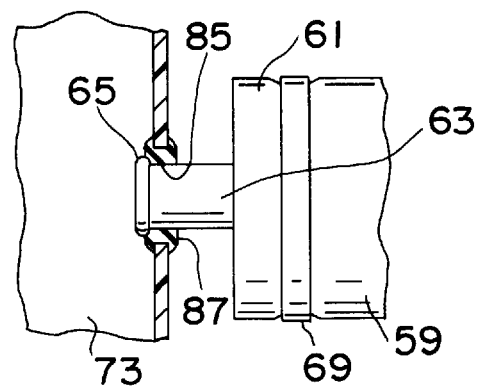
FIG. 5 is an enlarged fragmentary sectional view showing a preferred way for coupling one of the heart valve assemblies to one of the manifolds.

FIG. 5 shows one way in which the coupling of the fixture 46 to the manifold 73 accommodates valve-fixture assemblies of different lengths. FIG. 5 shows a portion of the manifold 73, and the manifold has an opening 85 and an annular seal or grommet 87 attached to the manifold around the opening 85. The seal 87, which is constructed of an elastomeric material, allows the rib 65 to be forced through the opening in the seal 87, and the seal sealingly engages the exterior surface of the neck 63. The depth of insertion of the neck 63 through the seal 87 can be varied so that the fixed manifolds 73 and 75 can accommodate valve-fixture assemblies of different overall lengths. Accordingly, it is only necessary to provide a valve-fixture assembly within certain length tolerances in order for it to be used in the system of FIG. 4. The rib 65 resists pull-out of the neck 63 from the seal 87. The construction shown for the manifold 73 at the opening 87 is typical for all of the openings and all of the manifolds 73, 75, 77 and 79.

Figure 6:
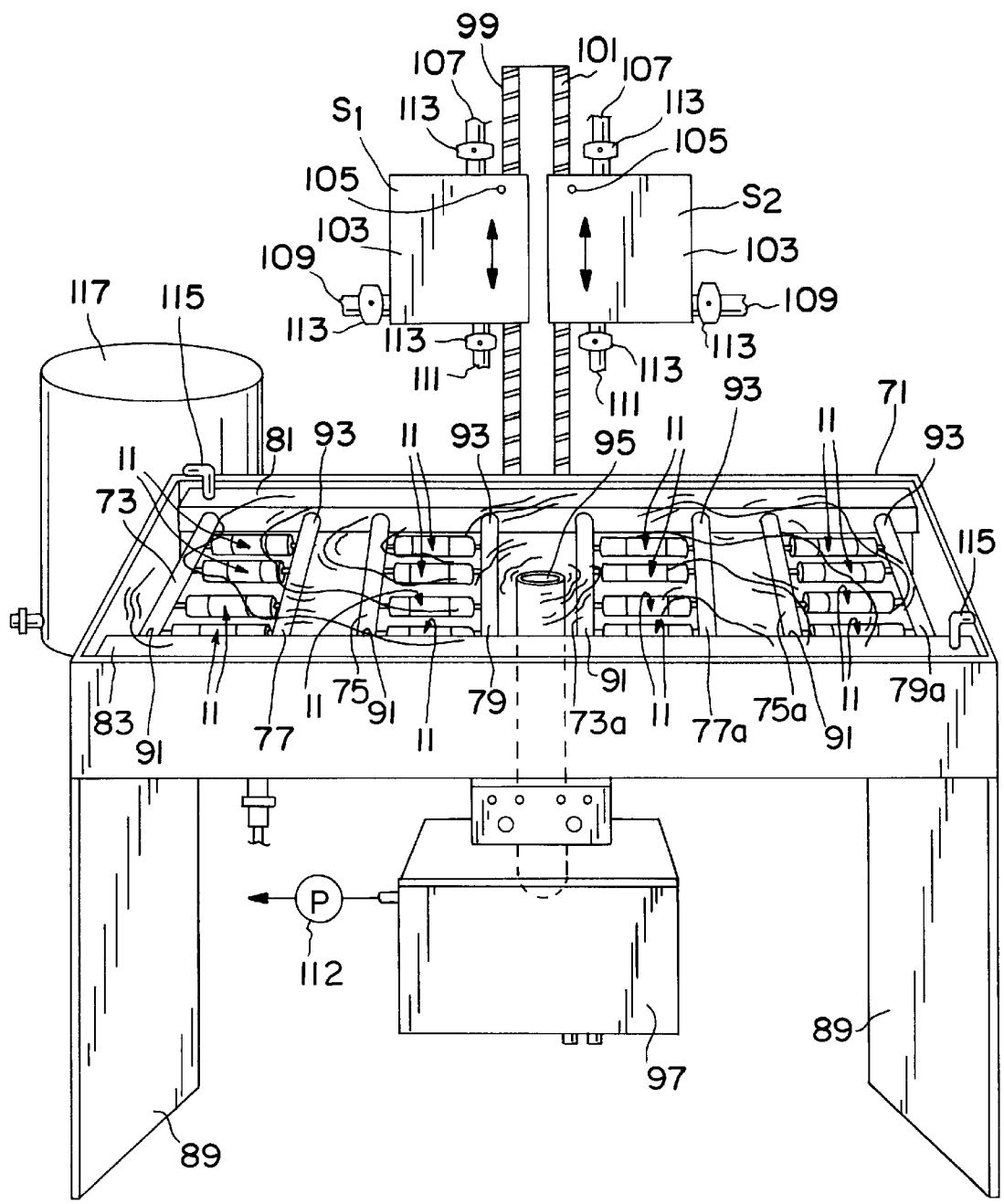
FIG. 6 is a perspective view illustrating an apparatus constructed in accordance with the teachings of this invention.

FIG. 6 shows one way in which the system of FIGS. 4 and 5 can be embodied. FIG. 6 shows the tank 71 supported above the floor by legs 89 having the inflow header 81 and the outflow header 83 suitably mounted within the tank. The inflow manifolds 73 and 75 and the outflow manifolds 77 and 79 have their opposite ends coupled to the headers 81 and 83. In addition, two additional sets of manifolds 73a, 77a, 75a and 79a also have their opposite ends coupled to the headers 81 and 83. The manifolds 73a, 75a, 77a and 79a may be identical to the manifolds 73, 75, 77 and 79. The end of each of the inflow manifolds 73, 75, 73a and 75a adjacent the outflow header 83 is plugged at locations 91, and the ends of the outflow manifolds 77, 79, 77a and 79a are plugged at locations 93 adjacent the inflow header 81. This allows the inflow header 81 to supply fixative fluid only to the inflow manifolds 73, 75, 73a and 75a and allows the outflow header 83 to supply fixative fluid only to the outflow manifolds 77, 79, 77a and 79a.

An overflow pipe 95 projects upwardly from the bottom of the tank 71 and extends downwardly through the bottom of the tank to a reservoir 97 for fixative solution, which in this embodiment is a glutaraldehyde solution. The top of the overflow pipe 95 is at the maximum desired level of fixative solution in the tank 71 and is above the upper surfaces of the valves 11 coupled across the associated manifolds. Preferably, the top of the pipe 95 is also above the upper surfaces of the headers 83 and 85 and the manifolds.

In this embodiment, the sources $S_1$ and $S_2$ are mounted for vertical movement on rotatable drive screws 99 and 101, respectively. The drive screws 99 and 101 are rotatably mounted on a suitable supporting structure, such as the tank 71, but these screws do not translate. Accordingly, by mounting the sources $S_1$ and $S_2$ on the screws 99 and 101 and retaining the sources against rotation, rotational movement of the drive screws 99 and 101 can be used to move the sources up and down as desired.

Each of the sources $S_1$ and $S_2$ comprises a container 103 having an inlet 105 for fixative solution, a vent 107, a outlet 109 and a drain 111. Valves 113 may be provided at the vents 107, the outlets 109 and the drains 111.

Initially, the containers 103 are supplied with fixative solution from the reservoir 97 by a pump 112, the discharge of which is coupled to the inlets 105. During this time, the valves 113 for the vents 107 are open, and the valves 113 for the drains 111 are closed. The fixative solution is supplied from the sources $S_1$ and $S_2$ to the headers 81 and 83, respectively, through the outlets 109 by opening of the associated valves 113. Air can be purged from the manifolds and the headers 81 and 83 through vents 115 on the headers 81 and 83, respectively, and these vents can be opened and closed as desired by stop cocks (not shown).

Fixative solution is supplied to the tank 71 from a drum 117. This can be accomplished either with a pump or by gravity flow.

Flow from the sources $S_1$ and $S_2$ is the result of the static head of the fixative solution in the sources. This static head can be varied as desired by moving the containers 103 upwardly and downwardly along the drive screws 99 and 101 and/or by varying the height of the fixative solution within each of the containers. Moreover, these head heights can be varied during fixation to change the differential pressures acting across the valve leaflets 15 and the tubular wall 13.

By elevating the source $S_1$ relative to the source $S_2$, the pressure in the inflow sections 17 will exceed the pressure in the outflow sections 19 to create a differential pressure across the valve leaflets tending to open them. This will allow the fixative solution to flow through the valve leaflets from the inflow section 17 to the outflow section 19. The leaflets 15 can be closed by changing the height of one or both of the sources $S_1$ and $S_2$ to provide a fluid pressure in the outflow sections 19 greater than the pressure in the inflow sections 17. If the direction of the differential fluid pressure across the leaflets is repeatedly reversed, dynamic fixation of the leaflets an be obtained. However, for dynamic fixation, it may be preferred to change the pressure of a compressible inert gas in each of the containers 103 rather than repeatedly varying the static head of the sources $S_1$ and $S_2$. Dynamic valve leaflet fixation is discussed in U.S. Pat. No. 5,279,612, issued Jan. 18, 1994, to Eberhardt, claims priority on U.S. patent application Ser. No. 366,375, filed on Jun. 9, 1989, now abandoned.

Although an exemplary embodiment of the invention has been shown and described, many changes, modifications and substitutions may be made by one having ordinary skill in the art without necessarily departing from the spirit and scope of this invention.

We claim:

1. A method of fixing a natural tissue heart valve which includes a tubular wall defining a passage and valve leaflets dividing the passage into an inflow section leading to the leaflets and an outflow section leading away from the leaflets with the leaflets being openable to allow flow from the inflow section to the outflow section, said method comprising:

attaching a first fixture to the inflow section to provide an inflow chamber, said first fixture having an inlet leading to the inflow chamber;

attaching a second fixture to the outflow section to provide an outflow chamber, said second fixture having an inlet leading to the outflow chamber;

subjecting the exterior of the valve to a fixative fluid at a first pressure, flowing fixative fluid under a second pressure through said inlet leading to the inflow chamber, and flowing fixative fluid under a third pressure through said inlet leading to the outflow chamber.

2. A method as defined in claim 1 wherein the valve has an annulus and the first-mentioned step of attaching includes providing a support ring about the inflow section with the support ring having a wavy edge positioned to support the annulus.

3. A method as defined in claim 1 including supporting the tubular wall of the inflow section against expansion as a result of the fixative fluid under pressure in the inflow section.

4. A method as defined in claim 1 wherein the first fixture includes an end wall, a support ring and an elastomeric sleeve and the end wall is coupled to the support ring by the elastomeric sleeve and the first-mentioned step of attaching includes inserting the inflow section into the support ring.

5. A method as defined in claim 1 wherein the first-mentioned step of attaching includes providing a support ring about the inflow section, folding tissue of the valve about an edge portion of support ring and clamping the folded tissue between an elastomeric sleeve and the support ring, and said first fixture includes an end wall coupled to the sleeve.

6. A natural tissue heart valve fixed in accordance with the method of claim 1.

7. A method according to claim 1 wherein said first pressure is approximately zero and said second and third pressures are greater than said first pressure.

8. A method according to claim 7 wherein the difference between said second and third pressures is substantially zero.

9. A method according to claim 7 wherein said third pressure is greater than said second pressure in an amount no greater than about 4 mm of mercury.

10. A method according to claim 9 wherein said third pressure is in the range of from about 20 to about 50 mm of mercury.

11. A method of fixing a natural tissue heart valve which include a tubular wall defining a passage and valve leaflets dividing the passage into an inflow section leading to the leaflets and an outflow section leading away from the leaflets with the leaflets being openable to allow flow from the inflow section to the outflow section, said method comprising:

coupling the inflow section to fixative fluid under pressure;

coupling the outflow section to fixative fluid under pressure;

immersing the valve in a bath of fixative solutions; and flowing fixative solution into the inflow section and the outflow section with the pressure of the fixative fluid in the outflow section being greater than the pressure of the bath acting on the valve to provide a desired differential pressure acting outwardly across the tubular wall of the outflow section and with the pressure of the fixative fluid in the inflow chamber being sufficient in relation to the pressure of the fixative fluid in the outflow section to create a desired differential pressure across the valve leaflets.

12. A method as defined in claim 11 wherein the differential fluid pressure across the outflow section is greater than the differential fluid pressure across the valve leaflets.

13. A method as defined in claim 12 wherein the differential fluid pressure across the outflow section is sufficient to enlarge the outflow section and the differential fluid pressure across the valve leaflets is no greater than about 4 mm of mercury.

14. A method as defined in claim 13 wherein the differential fluid pressure across the valve leaflets is substantially zero.

15. A method as defined in claim 11 including flowing fixative fluid from the inflow section to the outflow section.

16. A method as defined in claim 11 wherein the steps of coupling include coupling the inflow and outflow sections to first and second sources of fixative fluid, respectively.

17. A method as defined in claim 16 including changing the pressure of the fixative fluid supplied by at least one of said sources to the associated section.

18. A method as defined in claim 11 including supporting the tubular wall of the inflow section against expansion as a result of the fixative fluid under pressure in the inflow section.

19. A natural tissue heart valve fixed in accordance with the method of claim 11.

20. A method of fixing a plurality of natural tissue heart valves wherein each of the heart valves includes a tubular wall defining a passage and valve leaflets dividing the passage into an inflow section leading to the leaflets and an outflow section leading away from the leaflets with the leaflets being openable to allow flow from the inflow section to the outflow section, said method comprising:

coupling all of the inflow sections to a first manifold and all of the outflow sections to a second manifold;

subjecting the exterior of the valves to the action of a fixative fluid; and supplying fixative fluid under pressure through said first and second manifolds to the inflow and outflow sections, respectively.

21. A method as defined in claim 20 wherein the step of supplying includes supplying the fixative fluid from separate first and second sources to the first and second manifolds, respectively.

22. A method as defined in claim 21 including changing the elevation of at least one of the first and second sources to change the pressure of the fixative fluid supplied by such source to the associated manifold.

23. A method as defined in claim 21 wherein the step of subjecting includes immersing the valves in the fixative solution.

24. A natural tissue heart valve fixed in accordance with the method of claim 20.

25. A method of fixing a natural tissue heart valve which includes a tubular wall defining a passage and valve leaflets dividing the passage into an inflow section leading to the leaflets and an outflow section leading away from the leaflets with each of the inflow and outflow sections having an opening attached to a fluid source, said method comprising:

subjecting the exterior of the valve to a fixative fluid; and supplying fixative fluid under pressure through each of said openings into the associated section.

26. A method as defined in claim 25 including supporting the tubular wall of the inflow section against expansion as a result of the fixative fluid under pressure in the inflow section.

27. A method as defined in claim 25 wherein the pressures of the fixative fluid in the inflow and outflow sections are substantially equal.

28. A method as defined in claim 25 wherein the step of subjecting includes immersing the valve in a fixative solution and the method includes supporting the tubular wall of the inflow section against expansion as a result of the fixative fluid under pressure in the inflow section.

29. A natural tissue heart valve fixed in accordance with the method of claim 25.

* * * * *